(12) United States Patent
Wolfinbarger, Jr. et al.

(10) Patent No.: US 6,837,907 B2
(45) Date of Patent: Jan. 4, 2005

(54) METHOD FOR DEBRIDING BONE, AND BONE DEBRIDED THEREBY

(75) Inventors: Lloyd Wolfinbarger, Jr., Virginia Beach, VA (US); Robert K. O'Leary, Deltaville, VA (US); Louis Ford, Virginia Beach, VA (US); Alyce Linhurst Jones, Virginia Beach, VA (US)

(73) Assignee: LifeNet, Virginia Beach, VA (US)

( * ) Notice: Subject to any disclaimer, the term of this patent is extended or adjusted under 35 U.S.C. 154(b) by 18 days.

(21) Appl. No.: 10/108,804

(22) Filed: Mar. 27, 2002

(65) Prior Publication Data

US 2003/0014124 A1 Jan. 16, 2003

Related U.S. Application Data

(60) Provisional application No. 60/279,319, filed on Mar. 28, 2001.

(51) Int. Cl.$^7$ .............................................. A61B 19/00
(52) U.S. Cl. ....................................... 8/94.11; 9/94.1 R
(58) Field of Search ............................. 8/94.11, 94.1 R

(56) References Cited

U.S. PATENT DOCUMENTS

| | | | | |
|---|---|---|---|---|
| 4,946,792 | A | * | 8/1990 | O'Leary |
| 5,120,656 | A | * | 6/1992 | O'Leary |
| 5,125,837 | A | * | 6/1992 | Warrin et al. |
| 6,190,642 | B1 | * | 2/2001 | Dougherty et al. |

* cited by examiner

*Primary Examiner*—Margaret Einsmann
(74) *Attorney, Agent, or Firm*—Hale and Dorr LLP

(57) ABSTRACT

The invention is directed to a method of debriding bone including incubating the bone and associated soft tissue, with one or more debriding solutions where the debriding solution may include one or more alkaline solutions. Incubation is optionally carried out with one or more debriding agents including inert dry granular or particulate material including for example beads, and the granular phase of an alkaline agent, including for example granular sodium hydroxide. The incubating may be carried out with agitation. In another embodiment, the medullary canal of the bone is subjected to a positive pressure stream of debriding solution under conditions sufficient to loosen the associated soft tissue from the bone at the interface of the soft tissue and bone. In a further embodiment, the debriding solution is provided as a gel.

61 Claims, No Drawings

METHOD FOR DEBRIDING BONE, AND BONE DEBRIDED THEREBY

This application claims the benefit of Provisional Application Ser. No. 60/279,319 Mar. 28, 2001.

FIELD OF THE INVENTION

The invention relates to a process for efficiently removing soft tissue from bone to produce debrided bone for use in the production of clinical bone grafts. The soft tissue to be removed is primarily periosteum, a specialized connective tissue covering all of the bones of the body, muscle and connective tissue other than periosteum, as well as cartilage on the articulating ends of bones.

BACKGROUND OF THE INVENTION

Bone tissue is used in a wide variety of clinical applications to repair and/or replace defective or damaged bones. The bone used in these applications include whole or entire bones, sections of bones, and/or ground bone including bone chips. Such clinical applications include spinal fusions procedures, craniotomies, and repair of compound fractures of long bones. Demineralized cortico-cancellous bone chips and finely ground demineralized bone powders are used as fill materials where there is a bone defect, for example, in the repair of "holes" resulting from surgical procedures where removal of parts of a bone or bones or teeth.

Bone harvested from a cadaver is stored frozen until release criteria, for example microbiological/virological testing, are satisfied. At such time, the bone is thawed, debrided of excess soft tissues on the surface of the bone, bone marrow is removed from the cancellous bone space, and the bone is then cut into clinically usable grafts. As a preliminary step in the preparation of small bone grafts, soft tissues must be removed from the exterior surface of the bone in order to permit assessment of the "quality" of the bone. Bone from individual donors may not be suitable for the production of specific types of bone grafts, specifically load-bearing grafts such as the iliac crest wedge, and by visually inspecting the debrided bone it is possible to assess whether or not the bone will be suitable in the preparation of small bone grafts. Thus, removal of external soft issues such as the periosteum is important in the processing of bone into small bone grafts.

Prior art methods for removing soft tissue from bone include mechanically removing soft tissue and by enzymatic digestion. These methods are disadvantageous in that they are labor intensive, expensive, and also in the case of enzymatic digestion, may introduce the potential of contamination of the processed bone with immunogenic foreign proteins (the proteolytic enzymes) and/or associated potentially infectious agents associated with the extraction of the enzymes from animal species which might harbor infectious agents.

The invention overcomes the problems presented by the prior art methods by providing a simple and convenient method of debridement. The method also provides the additional advantage of inactivating infectious agents which may be associated with the bone tissue being processed, such infectious agents including bacteria, fungi, virus particles, and prions.

SUMMARY OF THE INVENTION

It is an object of the invention to provide a process for debriding bone by contacting the bone with a debriding solution, such debriding solution including one or more alkaline solutions, to loosen the soft tissue including periosteum and other associated soft tissues from the bone, thus facilitating the removal of such soft tissue from the bone. Such contacting may include incubating the bone with the debriding solution in a closed system. For example, the bone and solution may be incubated in a roller bottle. Another object of the invention is contacting the bone with a debriding solution and one or more debriding agents. Such incubation with a debriding agent may be simultaneous or sequential. Suitable debriding agents include for example, beads which beads are composed of, one or more of glass, ceramic, metal, plastic, polymer, and composites. The debriding agent may be any particulate matter sufficient to loosen and/or remove soft tissue from bone and includes for example, screws, set screws, ground glass, broken curved glass, dry alkaline chemicals used to form the debriding solution, for example dry NaOH.

It is an object of the invention to provide a process for debriding bone by subjecting the medullary canal of the bone to a positive pressure stream of debriding solution.

It is a further object of the invention to provide a process for debriding bone where the bone and debriding agent and/or debriding solution, are agitated. Suitable methods of agitating include agitating on a shaker table, revolving or rotating, for example the bone and solution/agent are placed in a roller bottle, and the roller bottle is rotated on a roller table, sonicating, centrifuging, and subjecting the bone and solution and/or agent to a pressure mediated stream of solution.

It is another object of the invention to provide a debriding solution including one or more permeation agents which facilitate permeation of the alkaline chemicals into the soft tissue and includes for example, one or more surfactants and detergents.

It is a further object of the invention to provide a debriding solution including one or more inactivating agents, such inactivating agents including one or more antibiotics, antimicrobials, antiviral agents, antifungals, and disinfectants, to inactivate any potential biological contaminants present in the tissue being processed.

It is an object of the invention to provide a process for debriding bone including removing the loosened soft tissue from the bone. Such removal includes for example, scraping the bone with mechanical means and/or wiping the bone, such mechanical means including for example a sterile brush, a household pot-scrubber, and a scraper. Such removal may optionally be performed with a removal liquid, such removal liquid may be provided as a stream, for example a low, medium or high velocity stream. Suitable removal liquids include water, the water optionally including one or more inactivating agents including for example one or more disinfectants, surfactants, detergents, and/or antibiotics.

A further object of the invention is to provide a process for the debridement of cadaveric human bone, and bone from nonhuman sources, having its periosteum ant other associated soft tissues intact which includes contacting the bone with one or more debriding solutions under conditions sufficient to loosen the periosteum and other soft tissues from the external surfaces of the bone, and thereafter removing the loosened soft tissue from the bone using for example, one or more mechanical means.

Another object of the invention is to provide a process for the debridement of cadaveric human bone, and bone from nonhuman sources, having its periosteum and other associated soft tissues intact which includes contacting the bone with one or more debriding solutions for a period of time at a temperature sufficient to loosen the periosteum and other soft tissues from the external surfaces of the bone, and thereafter removing the loosened soft tissue from the bone using for example one or more mechanical means, such mechanical means including for example scraping, scrubbing, wiping, and subjecting the external surfaces of the bone to a stream of pressurized removal liquid including for example one or more inactivating agents.

An object of the invention is to provide a process including a debriding solution that is a gel.

Another object of the invention is to provide a process where the gel is a reverse phase polymer.

A further object of the invention is to provide a process where the reverse phase polymer is PLURONIC®.

DETAILED DESCRIPTION OF THE PREFERRED EMBODIMENTS

I. Definitions

The below definitions serve to provide a clear and consistent understanding of the specification and claims, including the scope to be given such terms.

Alkaline Solution

By the term "Alkaline Solution" is intended a solution including one or more of sodium hydroxide, potassium hydroxide, ammonium hydroxide, lithium hydroxide, trisodium phosphate, tripotassium phosphate and triethanolamine, preferably at a concentration of from about 0.1 N to 1.0 N, or 0.1 M to about 25.0 M, more preferably at a concentration of from 0.1 M to 3.0 M.

Debriding Solution

By the term "debriding solution" is intended a liquid or gel optionally including one or more alkaline solutions, suitable debriding solutions including for example water, isotonic saline, and aqueous solutions of one or more of sodium hydroxide, potassium hydroxide, ammonium hydroxide, lithium hydroxide, trisodium phosphate, tripotassium phosphate and triethanolamine.

Inactivating Agent

By the term "inactivating agent" is intended for the purposes of the invention any agent that inactivates and/or kills any viral, bacterial, or fungal contamination, and/or inactivates prions. Suitable inactivating agents include for example one or more of a surfactant, a detergent, an alcohol, listerine, an antibiotic, an antiviral, and an antifungal. Preferred inactivating agents include non-denaturing anionic surfactants including for example n-lauroyl sarcosinate (NLS) and alcohols including for example 1-octanol. A preferred inactivating agent is 1% NLS, 10% 1-octanol in 0.05 M sodium acetate buffer at pH 4.3–4.9.

Debriding Agent

By the term "debriding agent" is intended for the purposes of the invention any solid matter of a shape and size sufficient to loosen soft tissue from the surfaces of the bone to be debrided. Suitable debriding agents include beads or particulate matter, for example beads and/or particulate matter of uniform or non-uniform size and/or shape, composed of for example, glass, metal, ceramic, plastic, polymer, composites, and/or solid alkaline agent for example NaOH. Suitable debriding agents include screws, set screws, nuts, bolts, broken glass, ground glass, curved broken glass, round beads, elliptical beads, biconcave beads, and faceted beads. Preferably debriding agents include solid NaOH and biconcave faceted beads, available from Hirschberg, Schutz & Co., where the bead weighs 0.5 g and has sixteen faceted, sharp, slanted surfaces, with a width of 7.7 mm and a height of 7.9 mm at a center point. Preferably, the debriding agent includes particles having a diameter of from about 0.1 to about 30 mm, preferably from about 1.0 to about 20 mm, more preferably from about 2.5 to about 15 mm, and most preferably from about 5.0 to about 9.0 mm.

Substantially Free from

By the term "substantially free from" is intended a debrided bone where any potential biological contaminants including for example bacteria particles, virus particles, fungi, and prions, are not detectable using detection mean known in the art at the time of filing of this application.

Allowash™

By the term "ALLOWASH™" solution is intended formulations available from LifeNet, Virginia Beach, Va. and disclosed in U.S. Pat. No. 5,820,581, and include solutions of polyoxethylene-4-lauryl ether (Brij-35), octylphenol-ethylene oxide (Nonidet P-40) and poly(ethylene glycol)p-nonyl-phenyl-ether (Nonoxynol-9). A 1× solution of ALLOWASH™ contains about 0.66 wt % Brij-35, about 0.02 wt % Nonidet P-40, and about 0.02 wt % Nonoxynol 9 in endotoxin free water.

Bone

By the term "bone" is intended for the purposes of the invention, allogenic, autogenic, and xenogenic bone. Preferably, the bone used is human cadaveric bone, and preferably includes the femur, tibia, humerus, fibula, ulna, and radius.

Soft Tissue

By the term "soft tissue" is intended tissue normally associated with bone including periosteum.

Permeation Agent

By the term "permeation agent" includes for the purposes of the invention one or more agents capable of facilitating permeation of the debriding solution into the soft tissue, and includes one or more of a surfactant, a detergent, and a surface active agent.

Gel Forming Material

By the term "gel forming material" is intended any polymer capable of gelling the desired debriding solution. Suitable polymers include reverse phase polymers including for example, PLURONIC®. Suitable polymers include methyl cellulose and carboxymethyl cellulose.

Debrided Bone

Bone debrided by the present process exhibits mechanical properties substantially similar to those exhibited by non-debrided bone, such mechanical properties including compressive strength, tensile strength, deformability, plasticity, and machine ability.

Agitation

By the term "agitation" is intended any method of increasing contact between the bone to be debrided and the debriding solution, and includes for example, shaking, for example using a shaker table, subjecting the bone and soft tissue to a pressure mediated stream of debriding solution, revolving the bone and debriding solution, optionally in the presence of a debriding agent, for example in a roller bottle on a roller table, at a rate of preferably from about 10 to about 200 revolutions per minute, more preferably from about 20 to about 100 revolutions per minute, and more preferably at about 60 revolutions per minute, sonication, and centrifugation.

II. Suitable debriding solutions include water, and alkaline solutions and may optionally include one or more cleansing agents, such cleansing agents including for example Allowash™ solution as described in U.S. Pat. No. 5,556,379, other surfactants, detergents, inactivating agents, permeation enhancers, surface active agents, and one or more alcohols.

Suitable cleansing agents include one or more surfactants, detergents and permeation enhancers, which cleansing agents are capable of facilitating permeation of the soft tissues by the debriding solution. Suitable alkaline solutions include, but are not limited to, sodium hydroxide, lithium hydroxide, ammonium hydroxide, saturated lime water, calcium hydroxide, trimethylammonium hydroxide, cupric or cuprous hydroxide, potassium hydroxide, triethanolamine, and tribasic phosphates such as $K_3PO_4$, $Na_3PO_4$, with sodium hydroxide, potassium hydroxide and tribasic phosphates being preferred.

The one or more debriding solutions including one or more alkaline solutions are employed under conditions that promote digestion of the organic components of soft tissues facilitating debridement of the bone without altering the physical and chemical characteristics of the underlying bone. Bone is composed of hydroxyapatite, a "crystalline" phase of calcium phosphate, which is insoluble at alkaline pH and is thus relatively inert to the alkaline solutions used to debride the soft tissues from the bone. For example, in the case of sodium hydroxide, the concentration of the sodium hydroxide can vary between about 0.1N and about 5N, preferably between about 0.5N and about 1N. The temperature can be anywhere in the range of from about 5° C. to about 65° C., preferably from about 25° C. to about 55° C. for routine processing, and optimally from about 37° C. to about 65° C., or 2° C. to about 10° C. where preferred debridement times are shorter or longer, respectively. The preferred temperature and concentration of alkaline solution, vary depending on the desired time interval used to loosen the soft tissue from the external surface of bone. Based on processing schedules, bone can be treated at reduced temperatures and alkaline solution concentrations overnight or at elevated temperatures and high concentrations of alkaline solutions for short periods of time, for example 30 minutes to 1 hour with 3N NaOH at 55° C. to 65° C. in the morning prior to initiation of the daily processing schedule, for example while the bone is being thawed from the frozen state. The debriding solution may optionally contain a variety of additives including surfactants, detergents, inactivating agents, cleansing agents, and gel-forming materials used to coat the bone.

Suitable contact times of the bone with the one or more debriding solutions including one or more alkaline solutions, are most preferably sufficient to loosen the attached soft tissues without digesting the osteoid material in the bone, and preferably for a period of time of from about 30 minutes to overnight. The desired contact time can be varied, depending on the concentration of alkaline solution and temperatures utilized to achieve the desired processing time appropriate to production needs. For example, if longer processing times are desired, the temperature may be lowered and/or the concentration of alkaline solution can be lowered, and/or incubation can be carried out without a debriding agent or with a mild debriding agent including for example round glass beads. Likewise, if shorter processing times are desired, the temperature and concentration can be increased and/or incubation can be carried out with a debriding agent, for example a sharp edged bead. In addition, application of the debriding solution including alkaline solution to specific areas of the bone can be controlled by applying the solution in a viscous gel of an appropriate biocompatible polymer including for example, pluronic, methyl cellulose, or mixed copolymers of polyglycolic/polylatic acid. Use of a debriding solution in a gel form facilitates application of the debriding solution including one or more alkaline solutions to those parts of the bone containing significant quantities of soft tissue to be debrided with restriction of application of the same solution to parts of the bone lacking significant quantities of soft tissue. Specifically, use of a reverse phase polymer including for example, pluronic polymer in a range of from 5 to 20 wt % with the debriding solution to provide a gelled debriding solution, has the additional advantage of being a liquid at colder temperatures, for example the temperature of a bone being thawed during early morning preparatory activities, but a viscous gel at warmer temperatures, for examples temperatures a bone might be held at following application of the debriding solution including the alkaline pluronic polymer mixture. For example, the alkaline pluronic polymer gel is "painted" onto the bone at those locations where soft tissue removal is most difficult to achieve or not applied where possible damage to the underlying bone would be undesirable.

In another embodiment of the invention, sterile air is injected under the periosteum, between the bone and the periosteum to facilitate separation of the periosteum from the bone surface prior to or in conjunction with mechanical debridement and to use a stream of removal solution, for example water, over the bone during the mechanical debridement following alkaline solution treatment in that the stream of water flowing over the bone facilitates removal of softened tissue and alkaline solutions. In general, alkaline solutions impart a feeling of "slickness" when the fingers are rubbed together or over treated tissues and thus absence of this feeling of "slickness" can be used to determine when the alkaline solution has been effectively removed from the debrided bone.

In accordance with a particular embodiment of the debridement process described herein, alkaline solution penetration can be enhanced by inclusion of a permeation enhancer. A permeation enhancer can be included in the debriding solution optionally including an alkaline solution to enhance accessibility of the alkaline solution into more hydrophobic domains of the tissue, for example lipid aggregates, and to facilitate solubilization and removal of fragments and molecular species of the tissue broken up or "dissolved" by the alkaline solution.

Suitable permeation enhancers include, but are not limited to, surface active agents and detergents which may include cationic, nonionic and anionic amphipathic or lipophilic agents; brij-35, nonoxynol-9, nonidet P-40, sodium lauryl sulfate, N-lauroylsarcosinate, dimthylsulfoxide, dimethyl formamide, propylene glycol, benzyl alcohol, glycerol monolaurate, isopropyl palmitate, isopropyl myristate, azacyclohexanes, lecithin, dimethylacetamide, and detergents in the Tween and Triton series and/or alcohols including isopropyl, ethanol, n-propyl and butyryl alcohols. Preferred permeation enhancers are anionic amphipathic detergents including for example sodium lauryl sulfate, N-lauroylsarcosinate, and/or isopropyl alcohol and pluronic polymer. The amount of permeation enhancer employed can vary depending on the quantity of soft tissue to be debrided, with suitable concentrations in the range of from about 3 mM to about 30 mM detergent and/or 70% alcohol in the debriding solution including one or more alkaline solutions. Similar compositions, described in Allowash™ technology, U.S. Pat. No. 5,556,379, and N-lauroylsarcosinate at pH values between about 4 and 6 are bactericidal and virucidal.

The alkaline/alcoholic solutions, may optionally contain one or more other components beneficial to the process, for example one or more inactivating agents, including for example one or more antibiotics and/or disinfecting agents. Suitable antibiotics include bacitracin, erythromycin, neomycin, tetracycline, polymyxin B sulfate, vinocomycin, lincomycin, streptomycins, chloromycetin, gentamicin, furosemide, immupenin, and penicillin's. Suitable preferred disinfectants include those which are soluble in alkaline aqueous solutions and are administered at concentrations known in the art to be germicidal, and include, but are not limited to, ethanol, isopropanol, 1-octanol, hydrogen peroxide (preferably as a 3% to 10% solution), cetyl alcohol, and benzalkonium chloride. Disinfectants such as sodium hypochlorite should be avoided due to the potential for gas emission in alkaline solutions. Preferably, the disinfectant is isopropanol, 1-octanol, or ethanol, and are employed at a concentration of from about 30 to about 70%, and N-lauroylsarcosinate at a pH of from 4 to 6. Alcoholic concentrations of 100% should be avoided due to a potential for precipitation of proteins in the soft tissue making the soft tissue more difficult to digest and debride from the bone. Optimum amounts of other disinfectants, for example LISTERINE®, can be readily determined by one of ordinary skill in the art to which the present invention pertains without undue experimentation.

III. A preferred embodiment of the invention includes contacting the bone to be debrided in a closed system, for example a roller bottle, with an amount of debriding agent sufficient to cover the bone being processed. The debriding agent is preferably a particulate solid material, more preferably a sharp edged particulate material and/or a granular phase of the alkaline solution, of a size and shape sufficient to loosen the associated soft tissue from the bone and of sufficient size to be excluded from the medullary canal of the bone during processing. Debriding solution, preferably including one or more alkaline solutions, is added to the bone and debriding agent in an amount sufficient to cover the bone and debriding agent. The addition of debriding solution may be prior to, simultaneous with or subsequent to the addition of bone and debriding agent. The debriding agent preferably includes a mixture of a granular phase of the alkaline solution, for example solid, dry, NaOH. The bone including debriding agent and debriding solution is then incubated under conditions sufficient to loosen the soft tissue from the bone. Incubation may optionally include agitation including for example shaking, rotating, sonicating, centrifuging, and subjecting the bone to a pressurized stream of solution. Rotating, for example, can be carried out using a roller bottle which can be rotated on a roller table, preferably at about 10 to about 100 revolutions per minute, more preferably from about 20 to about 80 revolutions per minute, and most preferably at about 60 revolutions per minute. The roller bottle preferably includes means to ensure constant movement of the debriding agent, and/or debriding solution, and bone, such means including for example, baffles provided on the interior surface of the roller bottle.

IV. An embodiment of the invention includes a pressurized aqueous debridement solution delivery process. In this embodiment the liquid or gaseous debridement solution is transferred from within the medullary canal of the bone to the interface of the bone and associated soft tissue. The debridement solution penetrates the skeletal tissue by passing through the sharpey's fibres, haversian canals, volkman canals and other foramen of the cortical bone. The penetrating pressurized debridement solution exits as droplets or a fine spray of solution under the attached soft tissues on the outer surface of the undebrided bone. This process is preferably applied to bones including a femur, tibia, humerus, fibula, ulna, and radius. The transfer of the debriding solution is accomplished by subjecting the medullary canal of the bone to a positive pressure stream of the debriding solution. The debriding solution physically lifts the soft tissue off the external surface of the bone, thus loosening the adhering soft tissue from the bone. Depending on the composition of the debriding solution, the debriding solution may also chemically lift the soft tissue from the external surface of the bone. Suitable debriding solutions for use in this method include for example one or more of water and isotonic saline, at a pressure of from about 100 kPa to about 1000 kPa, for a period of time of from about 10 minutes to about 120 minutes, preferably from about 15 minutes to about 60 minutes, and more preferably from about 15 to about 30 minutes, preferably at ambient temperature. The debridement solution may include one or more alkaline solutions preferably including for example NaOH at a concentration of from about 0.5 to about 5.0 M. The debriding solution may optionally contain one or more of a surfactant, a permeation enhancer, an inactivating agent, a proteolytic enzyme, an antibiotic, an antiviral, and an antifungal. After the soft tissues have been loosened using the pressurized process, the bone may then optionally be subjected to incubation with one or more debriding solutions and/or debriding agents. Thereafter, any remaining soft tissue is removed. Preferably, this is accomplished by subjecting the medullary canal of one end of the bone to a positive pressure stream and closing the medullary canal at the other end of the bone, thus causing the positive pressure stream to exit the bone at the interface of the exterior surface of the bone and the associated soft tissue, thereby loosening the soft tissue.

V. Another embodiment of the invention includes contacting the bone with a debriding solution and debriding agents where the debriding agents include one or more of a granular phase of an alkaline agent and optionally one or more inert debriding agents, preferably a sharp edged bead for example composed of polyallyl diglycol carbonate polymer, glass, coarse sand, plastic, metal, composite, and stainless steel. Preferably, a mixture of dry inert debriding agent and dry alkaline granules are added to a closed system, for example to a roller bottle, and the wet bone is added. The wet bone, dry granules, inert debriding agent, and an amount of water sufficient to produce a concentrated alkaline solution for example, from about a 10.0 to about a 30.0 M solution, preferably about a 20.0 M solution, and the system is then sealed and rotated for example preferably at about 10 to about 100 revolutions per minute, more preferably from about 20 to about 80 revolutions per minute, and most preferably at about 60 revolutions per minute until a temperature of about 35° C. to about 45° C., preferably about 40° C. is achieved, for example for a time period of from about 1.0 minutes to about 30 minutes, preferably from about 2.0 minutes to about 20.0 minutes, and more preferably for about 5.0 minutes. Thereafter, sterile water is added to the bottle to dilute the alkaline solution to a desired molarity, for example from about 0.5 to about 5.0 M, preferably diluted to about 2.0 M. The alkaline solution is then incubated with the bone for a time period of from about 10 minutes to about 24 hours, preferably from about 20 minutes to about 10 hours, and more preferably for about 1 hour. The bone is then removed from the alkaline solution and any remaining soft tissue is removed.

VI. An additional embodiment of the invention includes first contacting the bone with a gelled debriding solution under conditions sufficient to loosen the associated soft tissue from the bone. The gelled solution is preferentially delivered to desired areas of the surface of the bone being processed. For example, gelled debriding solution is preferentially delivered to areas of the bone having greater amounts of associated soft tissue. After, the soft tissue is sufficiently loosened, the bone is processed according to the invention. For example, thereafter any remaining loosened soft tissue is removed mechanically and/or removed with the use of a pressurized stream of removal liquid. Alternatively, the bone may then be incubated with one or more debriding solutions with or without one or more debriding agents. Thereafter, any remaining associated soft tissue may be removed for example using mechanical means or a pressurized stream of removal liquid.

The following examples are illustrative of the inventive bone debridement process.

EXAMPLE 1

A whole left or right ilium, which has been harvested under aseptic conditions in accordance with accepted practice and from which excess associated soft tissues have been removed prior to transport to the processing facility and frozen for storage until proper release criteria have been satisfied, is thawed at least to the point of thawing of externally associated soft tissue, for example, the bone need not be thawed completely prior to initiation of incubation with one or more debriding solutions including one or more alkaline solutions. The bone to be debrided is placed into a debriding solution including 1.0 N NaOH and Allowash™ solution at a concentration of 0.01× at a volume adequate to cover the bone. The temperature is maintained at 60° C. for one to three hours, or until the soft tissue is visibly softened. At this time, the bone is removed from the debriding alkaline solution, sterile air is injected between the periosteum and bone, and the bone is placed under a stream of sterile slow flowing water and mechanically debrided using a commercially available plastic "pot scrubber". All processing is performed under aseptic conditions in order to maintain sterility of the bone. Associated articular cartilage is loosely associated with the underlying bone structure and is then carefully removed in large pieces by mechanically pulling from the bone and removed therefrom.

EXAMPLE 2

A whole left or right femur, which has been harvested under aseptic conditions in accordance with accepted practice and from which excess associated soft tissues have been removed prior to transport to the processing facility and frozen for storage. When proper release criteria have been satisfied, the tissue is thawed prior to initiation of debridement. The bone to be debrided is placed into a debriding solution including an alkaline solution of 0.5N NaOH containing N-lauroylsarcosinate at a concentration of 0.01 wt % and 30% v:v isopropanol, in a volume adequate to cover the bone. The temperature is maintained at 10° C. to 20° C. for 12 to 18 hours, or until the soft tissue is visibly softened. At this time, the bone is removed from the debriding solution and placed into a roller bottle containing glass bead having a diameter of from 1 to 4 mm, and N-lauroylsarcosinate in an aqueous solution buffered to between pH 4 and 6, and preferably at pH 5 to 5.6. The bone is rolled in the bottle at a rate of 60 rpm until the associated soft tissue has been removed. The bone is then removed and washed exhaustively to remove all processing reagents and is then prepared for freeze-drying and/or packaging in the hydrated state. All processing is performed under aseptic conditions in order to maintain sterility of the bone. Associated articular cartilage will be found to be loosely associated with the underlying bone structure and may be carefully removed in large pieces by mechanically pulling from the bone and removed therefrom. Once the associated soft tissues have been removed, the whole bone may be further processed using known art, for example, as described in U.S. Pat. No. 5,556,379, to remove associated bone marrow contained in the interior of the bone.

EXAMPLE 3

A whole left or right femur, which has been harvested under aseptic conditions in accordance with accepted practice and from which excess associated soft tissues have been removed prior to transport to the processing facility and frozen for storage until proper release criteria have been satisfied, is thawed prior to initiation of debridement. The bone to be debrided is covered with a debriding solution in the form of a gel, which is a viscous alkaline solution of 0.5 N NaOH and Allowash® solution at a concentration of 0.01× and 30% v:v isopropanol, and one or more gelling polymers including methylcellusolve and alginate, in a volume adequate to cover the bone. The bone is then wrapped in a commercially available plastic wrap to restrict water evaporation and incubated in a humidified chamber at a temperature from 10° C. to 20° C. for from 3 to 18 hours, or until the soft tissue visibly softened. At this time, the bone is removed from the plastic wrappings and placed under a stream of slow flowing water and mechanically debrided using a commercially available plastic "pot scrubber". All processing is performed under aseptic conditions in order to maintain sterility of the bone. Associated articular cartilage is loosely associated with the underlying bone structure and is carefully removed in large pieces by mechanically pulling it from the bone. Thereafter, the bone may be further processing using known methods, for example including those described in U.S. Pat. No. 5,556,379, to remove associated bone marrow contained in the interior of the bone.

EXAMPLE 4

A whole left or right femur, which has been harvested under aseptic conditions in accordance with accepted practice and from which excess associated soft tissues have been removed prior to transport to the processing facility and frozen for storage until proper release criteria have been satisfied, is thawed prior to initiation of debridement. The bone is then covered with a gelled debriding solution which is an alkaline solution consisting of 0.5 N NaOH and Allowash™ solution at a concentration of 0.01× and 30% v:v isopropanol, and methylcellusolve or alginate, as the gelling polymer, in an amount adequate to cover the bone. The bone is then placed into a glass or plastic roller bottle and glass beads in a size range of from 1 mm to 600 mm are added in an amount sufficient to cover the bone. The bottle is closed and placed onto a roller assembly and rolled at from 30 to 60 rpms, at a temperature at from 10° C. to 20° C. for a period of time of from 3 to 18 hours or until the soft tissue is visibly softened and removed. At this time, the bone was placed in a second bottle and smaller glass beads in a size range of from 0.01 mm to 1 mm are added in an amount adequate to cover the bone, along with antibiotics and 70% isopropanol, to affect a fine polishing of the essentially debrided bone. Any soft tissue remaining is then removed using a stream of slow flowing water and mechanically debrided using a commercially available plastic "pot scrubber". All processing is performed under aseptic conditions in order to maintain sterility of the bone. Associated articular cartilage is loosely associated with the underlying bone structure and is carefully removed in large pieces by mechanically pulling it from the bone. Thereafter, the bone may be further processing using known methods, for example including those described in U.S. Pat. No. 5,556,379, to remove associated bone marrow contained in the interior of the bone.

Although the invention has been described with reference to particular means, materials and embodiments, it is to be understood that the invention is not limited to the particulars disclosed and extends to all equivalents within the scope of the claims.

What is claimed is:

1. A process for debriding bone including soft tissue, comprising: contacting said bone with one or more debriding solutions under conditions sufficient to loosen said soft tissue from said bone to produce a first processed bone; and removing said soft tissue from said first processed bone to produce a debrided bone, wherein said debriding solutions are free from proteolytic and collagen-digesting enzymes.

2. The process of claim 1, said debriding solution comprising one or more alkaline solutions.

3. The process of claim 2, said alkaline solution comprising one or more alkaline members selected from the group consisting of: sodium hydroxide, potassium hydroxide, ammonium hydroxide, lithium hydroxide, trisodium phosphate, tripotassium phosphate and triethanolamine.

4. The process of claim 1, said contacting, comprising: contacting said bone with one or more gelled debriding solutions, said gelled debriding solution comprising one or more alkaline solutions, under conditions sufficient to loosen said soft tissue from said bone.

5. The process of claim 3, wherein said alkaline solution is formed by first adding said one or more alkaline members to said bone, where said one or more alkaline members is dry, to form a dry mixture; adding water to said dry mixture, said water in an amount sufficient to form an alkaline solution at a concentration of from 5.0 to 25.0 M over an incubation period, to form an alkaline mixture; incubating said alkaline mixture for an incubation time of from 2 minutes to 20 minutes to form an incubated mixture; further adding water to said incubated mixture in an amount sufficient to decrease concentration of said incubated mixture to a concentration of from 0.1 to 5.0 M to form a dilute alkaline solution, and second incubating said dilute alkaline solution with said bone for a time period sufficient to loosen said soft tissue.

6. The process of claim 1, said bone comprising a medullary canal, and said contacting, comprising: subjecting said medullary canal of said bone to a positive pressure stream of said debriding solution under conditions sufficient to loosen said soft tissue from an external surface of said bone.

7. The process of claim 6, said debriding solution comprising sterile isotonic saline.

8. The process of claim 6, said debriding solution comprising sterile water.

9. The process of claim 7, said positive pressure stream is at a pressure of from 100 kPa to 1000 kPa.

10. The process of claim 8, said subjecting is carried out for a period of time of from 10 minutes to 60 minutes.

11. The process of claim 1, said contacting comprising contacting for a period of time of from 30 minutes to 18 hours.

12. The process of claim 1, said contacting comprising contacting at a temperature of from 5° C. to 65° C.

13. A process for debriding bone including soft tissue comprising contacting said bone with one or more debriding solutions under conditions sufficient to loosen said soft tissue from said bone to produce a first processed bone, and removing said soft tissue from said first processed bone to produce a debrided bone, wherein said debriding solution comprises one or more alkaline solutions of concentration from 0.1 N to 1.0 N, and wherein said alkaline solutions comprise one or more alkaline members selected from the group consisting of: sodium hydroxide, potassium hydroxide, ammonium hydroxide, lithium hydroxide, trisodium phosphate, tripotassium phosphate and triethanolamine.

14. The process of claim 13, wherein said debriding solution comprises one or more alkaline solutions of concentration from 0.1 M to 25.0 M.

15. The process of claim 13, wherein said debriding solution comprises one or more alkaline solutions of concentration from 0.5 M to 20.0 M.

16. A process for debriding bone including soft tissue comprising contacting said bone with one or more debriding solutions under conditions sufficient to loosen said soft tissue from said bone to produce a first processed bone, and removing said soft tissue from said first processed bone to produce a debrided bone, wherein said removing step comprises injecting air between said soft tissue and said bone and subjecting said bone and said soft tissue to a flow of aqueous removal solution.

17. The process of claim 1, said debriding solution further comprising one or more permeation enhancers.

18. The process of claim 17, said permeation enhancer comprising a surface-active agent.

19. The process of claim 1, said debriding solution further comprising one or more inactivating agents.

20. The process of claim 19, said inactivating agent is an alcohol.

21. The process of claim 1, said removing comprising: mechanically removing said soft tissue from said bone using mechanical means.

22. The process of claim 16, wherein said removing step comprises mechanically removing said soft tissue from said bone using a scraper.

23. A process for debriding bone including soft tissue comprising contacting said bone including soft tissue with one or more debriding agents under conditions sufficient to loosen said soft tissue from said bone to produce a first processed bone, and removing said soft tissue from said first processed bone to produce a debrided bone, wherein said debriding agents comprise a granular alkaline agent.

24. The process of claim 6, further comprising after said step of subjecting, mechanically removing said soft tissue from said bone using mechanical means.

25. The process of claim 24, said mechanical means comprising a pot scrubber.

26. The process of any one of claim 1, 6, 21, or 16, wherein any one or more of said steps of removing, mechanically removing, injecting, and subjecting, is performed simultaneously or sequentially.

27. The process of claim 16, said aqueous removal solution comprises sterile endotoxin-free deionized/distilled water.

28. The process of claim 21, said mechanically removing, comprising: scraping said first processed bone under a flow of aqueous removal solution.

29. The process of claim 1, said one or more debriding solutions comprise a gelled solution.

30. The process of claim 29, said gelled solution comprising one or more members selected from the group consisting of a polymer and a thixotropic agent.

31. The process of claim 30, said polymer comprising one or more polymers selected from the group consisting of cellulose, methyl cellulose and carboxy methyl cellulose.

32. A process for debriding bone including soft tissue, comprising: contacting said bone including soft tissue with one or more debriding agents under conditions sufficient to loosen said soft tissue from said bone to produce a first processed bone; and removing said soft tissue from said first processed bone to produce a debrided bone, wherein said debriding agents are free from proteolytic and collagen-digesting enzymes.

33. A process for debriding bone including soft tissue, comprising: contacting said bone including soft tissue with one or more debriding agents and one or more debriding solutions, under conditions sufficient to loosen said soft tissue from said bone to produce a first processed bone; and removing said soft tissue from said first processed bone to produce a debrided bone, wherein said debriding agents and debriding solutions are free from proteolytic and collagen-digesting enzymes.

34. The process of any one of claim 1, 6, 32 or 33, said bone comprising one or more members selected from the group consisting of allogenic bone, autogenic bone and xenogenic bone.

35. The process of claim 34, said bone comprising allogenic bone.

36. The process of claim 35, said allogenic bone is human cadaveric bone.

37. The process of claim 36, said bone is frozen, thawed, or partially thawed.

38. A process for debriding bone including soft tissue comprising contacting in a closed container said bone including tissue with one or more debriding agents under conditions sufficient to loosen said soft tissue from said bone to produce a first processed bone, and removing said soft tissue from said first processed bone to produce a debrided bone.

39. The process of claim 23 or 38 said debriding agent further comprises inert beads.

40. The process of claim 39, said beads comprising one or more materials selected from the group consisting of an inorganic material and an anorganic material.

41. The process of claim 40, said inorganic material comprises one or more materials selected from the group consisting of glass, ceramic, amorphous, metal, plastic, and crystalline.

42. The process of claim 23 or 38, said granular alkaline agent comprising dry sodium hydroxide.

43. A process for debriding bone including soft tissue comprising contacting in a closed container said bone including soft tissue with one or more debriding agents and one or more debriding solutions, under conditions sufficient to loosen said soft tissue from said bone to produce a first processed bone, and removing said soft tissue from said first processed bone to produce a debrided bone.

44. The process of any one of claim 43, 38, or 23 said closed container comprising a rollable sealable bottle.

45. The process of claim 44, said rollable sealable bottle comprising one or more materials selected from the group consisting of glass and plastic.

46. The process of claim 44, said rollable sealable bottle comprises baffles provided on an interior surface thereof.

47. The process of claim 39, said beads comprise one or more beads of a size of from 0.01 mm to 100 mm in diameter.

48. The process of claim 47, said beads comprise one or more beads of a size of from 0.1 mm to 10 mm in diameter.

49. A process for debriding bone including soft tissue comprising contacting said bone including soft tissue with one or more debriding agents and one or more debriding solutions, under conditions sufficient to loosen said soft tissue from said bone to produce a first processed bone, and removing said soft tissue from said first processed bone to produce a debrided bone, wherein said debriding agents comprise a granular alkaline agent.

50. A process for debriding bone including soft tissue comprising contacting in a closed container said bone with one or more debriding solutions under conditions sufficient to loosen said soft tissue from said bone to produce a first processed bone, and removing said soft tissue from said first processed bone produce a debrided bone.

51. The process of any one of claim 1, 6, 32, or 33, said contacting is carried out from 30 minutes to 18 hours.

52. A process for debriding bone including soft tissue comprising contacting said bone including soft tissue with one or more debriding agents under conditions sufficient to loosen said soft tissue from said bone to produce a first processed bone, and removing said soft tissue from said first processed bone to produce a debrided bone, wherein said contacting comprises agitating said bone with said one or more debriding agents, and wherein said agitating comprises rolling.

53. A process for debriding bone including soft tissue comprising contacting said bone including soft tissue with one or more debriding agents and one or more debriding solutions, under conditions sufficient to loosen said soft tissue from said bone to produce a first processed bone, and removing said soft tissue from said first processed bone to produce a debrided bone, wherein said contacting comprises agitating said bone with said one or more debriding agents, and wherein said agitating comprises rolling.

54. The process of claim 52 or 53 said rolling is performed at a rate of from 10 to 100 revolutions per minute.

55. The process of claim 7, said sterile isotonic saline exits said bone at an interface of said bone and said soft tissue, where said soft tissue is loosened from said bone to produce a first debrided bone; and removing loosened soft tissue from said first debrided bone to produce debrided bone.

56. The process of any one of claim 1, 6, 32, or 33, further comprising treating said debrided bone with a cleansing solution to produce a cleansed bone.

57. The process of claim 56, said cleansing solution is at a pH of from 4 to 7.

58. The process of claim 57, said cleansing solution comprising N-lauroylsarcosinate.

59. The process of claim 58, said N-lauroylsarcosinate is at a concentration sufficient to inactivate one or more of bacterial, viral, microbial, fungal and prion contamination.

60. The process of claim 58, said N-lauroylsarcosinate is at a concentration of from 0.001 mM and 100 mM.

61. The process of claim 55, said step of removing comprising subjecting said first debrided bone to a stream of removal solution.

* * * * *